(12) United States Patent
Ball et al.

(10) Patent No.: US 8,827,904 B2
(45) Date of Patent: Sep. 9, 2014

(54) AUTOMATIC PARAMETER STATUS ON AN IMPLANTABLE MEDICAL DEVICE SYSTEM

(75) Inventors: James J. Ball, Saint Paul, MN (US); Sean B. McAdams, Minneapolis, MN (US); Chris T. House, Pine Island, MN (US)

(73) Assignee: Medtronic, Inc., Minneapolis, MN (US)

( * ) Notice: Subject to any disclaimer, the term of this patent is extended or adjusted under 35 U.S.C. 154(b) by 1314 days.

(21) Appl. No.: 11/217,028

(22) Filed: Aug. 31, 2005

(65) Prior Publication Data

US 2007/0060797 A1    Mar. 15, 2007

(51) Int. Cl.
| | |
|---|---|
| A61B 5/00 | (2006.01) |
| A61B 5/05 | (2006.01) |
| A61N 1/00 | (2006.01) |
| A61N 1/36 | (2006.01) |
| A61N 1/37 | (2006.01) |
| A61N 1/372 | (2006.01) |
| G08B 21/02 | (2006.01) |
| G06F 19/00 | (2011.01) |
| G08B 21/00 | (2006.01) |

(52) U.S. Cl.
CPC .......... *A61N 1/37252* (2013.01); *A61B 5/0031* (2013.01); *A61N 1/36* (2013.01); *A61B 5/4875* (2013.01); *A61N 1/3702* (2013.01); *G06F 19/34* (2013.01); *A61B 5/6869* (2013.01); *G06F 19/3418* (2013.01); *A61B 5/0002* (2013.01); *A61B 5/746* (2013.01); *G06F 19/3412* (2013.01); *G08B 21/0211* (2013.01); *A61B 5/686* (2013.01)
USPC .......... 600/300; 607/1; 607/2; 607/60; 705/2; 705/3; 340/870.01; 340/539.12; 600/547

(58) Field of Classification Search
CPC ... A61N 1/36; A61N 1/3702; A61N 1/37252; A61B 5/0002; A61B 5/686; A61B 5/6869; A61B 5/0031; A61B 5/746; A61B 5/4875; G08B 21/0211; G06F 19/34; G06F 19/3418; G06F 19/3412
USPC .......... 600/300–301, 547; 128/903–905, 920; 607/1, 2, 6, 60; 340/870.01, 539.12; 705/2–3
See application file for complete search history.

(56) References Cited

U.S. PATENT DOCUMENTS

| | | |
|---|---|---|
| 5,404,877 A | 4/1995 | Nolan et al. |
| 6,599,250 B2 | 7/2003 | Webb et al. |

(Continued)

FOREIGN PATENT DOCUMENTS

WO    WO0197907 A2    12/2001

OTHER PUBLICATIONS

International Search Report, PCT/US2006/033459, Jan. 17, 2007, 6 Pages.

*Primary Examiner* — William Thomson
*Assistant Examiner* — Marie Archer
(74) *Attorney, Agent, or Firm* — Michael C. Soldner

(57) ABSTRACT

A method and apparatus for providing status of a parameter that includes detecting an alert level of a parameter monitored by an implanted medical device, transmitting data corresponding to the detected alert level from the implanted medical device to an external monitor, scheduling a follow-up interrogation session after receiving transmitted data corresponding to the detected alert level, and retrieving updated data from the implanted medical device corresponding to the monitored parameter during the follow-up interrogation session.

13 Claims, 5 Drawing Sheets

(56) References Cited

U.S. PATENT DOCUMENTS

| | | |
|---|---|---|
| 6,694,177 B2 * | 2/2004 | Eggers et al. ............... 600/509 |
| 6,957,107 B2 * | 10/2005 | Rogers et al. ................ 607/60 |
| 7,009,511 B2 * | 3/2006 | Mazar et al. ................. 340/531 |
| 7,261,691 B1 * | 8/2007 | Asomani ...................... 600/300 |
| 7,265,676 B2 * | 9/2007 | Gordon et al. ............. 340/573.1 |
| 2003/0144711 A1 | 7/2003 | Pless et al. |
| 2004/0122488 A1 * | 6/2004 | Mazar et al. .................... 607/60 |
| 2005/0288738 A1 * | 12/2005 | Bange et al. .................... 607/60 |
| 2006/0017575 A1 | 1/2006 | McAdams |
| 2006/0017576 A1 | 1/2006 | Gordon et al. |
| 2006/0064136 A1 | 3/2006 | Wang |

* cited by examiner

AUTOMATIC PARAMETER STATUS ON AN IMPLANTABLE MEDICAL DEVICE SYSTEM

FIELD OF THE INVENTION

The present invention relates generally to implantable medical device systems and more particularly to an implantable medical device system and method for providing the status of a monitored parameter.

BACKGROUND OF THE INVENTION

A variety of implantable medical devices (IMDs) are commercially available for monitoring physiological signals. Such devices can be configured for delivering therapies, such as cardiac pacemakers and defibrillators, hemodynamic monitors, drug delivery devices, insulin monitors and pumps, neurostimulators, and muscle stimulators. These devices may detect clinically serious or life-threatening conditions related to physiological events or conditions. Such devices are also typically enabled to perform self-diagnostic tests or otherwise monitor device performance issues, such as battery life-expectancy, electrical lead impedance, frequency of delivered therapies, and so on. The advanced capabilities of IMDs in detecting physiological or device-related conditions that may warrant careful monitoring, clinical attention or even emergency care has motivated the addition of real time patient notification features to IMD systems.

Home monitors are external devices that can communicate with the IMD to retrieve data relating to device performance or physiological conditions. The use of home monitors for displaying or broadcasting a patient warning or notification has been proposed, such that the patient is aware of a condition that warrants further monitoring or attention. The home monitor is generally coupled to a communication network to transmit IMD data via the communication network to a remote patient management center. Health care professionals can thereby respond appropriately to the device-related and physiological data retrieved. Interrogation of the IMD by the home monitor and transfer of data to the remote patient management center can occur on a scheduled, periodic basis.

The IMD may be enabled to transmit data to the home monitor upon detecting a triggering event corresponding to a predetermined alert condition. A real-time warning alerts the patient that a condition requiring medical attention or warranting close monitoring or action by the patient has been detected. The home monitor may display a notification of the alert condition to the patient or other caregiver and/or transmit the data to the remote patient management center. However, further updates of the parameter causing the alert condition are generally not be available. The patient or clinician is not notified if the alert condition persists for a period of time or if the alert condition is no longer present. Updated data may not be remotely retrieved from the IMD until another triggering event, the next scheduled interrogation session or until a clinician manually schedules an interrogation.

BRIEF DESCRIPTION OF THE DRAWINGS

Aspects and features of the present invention will be readily appreciated as the same becomes better understood by reference to the following detailed description when considered in connection with the accompanying drawings, wherein.

DETAILED DESCRIPTION

In the following description, references are made to illustrative embodiments for carrying out the invention. It is understood that other embodiments may be utilized without departing from the scope of the invention.

The present invention is directed toward providing an up-to-date status of a parameter by an IMD. In the past, data stored by an IMD was generally retrieved only during an interrogation session during a clinical office visit. With the development of remote patient management systems, an IMD can be interrogated on a more frequent, scheduled basis according to an interrogation schedule programmed into the remote patient management system. An unscheduled data transmission may occur when the IMD detects a predefined alert level of a monitored parameter. Since the transmission occurs once in response to an alert level detection, the duration that the monitored parameter remains at an alert level and whether the monitored parameter returns to a non-alert level may remain unknown until the next scheduled interrogation. The invention is directed toward scheduling additional IMD interrogations by the external monitor so that updated parameter values can be retrieved following detection of an alert level. An up-to-date status of the monitored parameter is thereby available for the patient and/or clinician, irrespective of any previously programmed interrogation session schedule stored within the remote patient management system.

Figure 1:
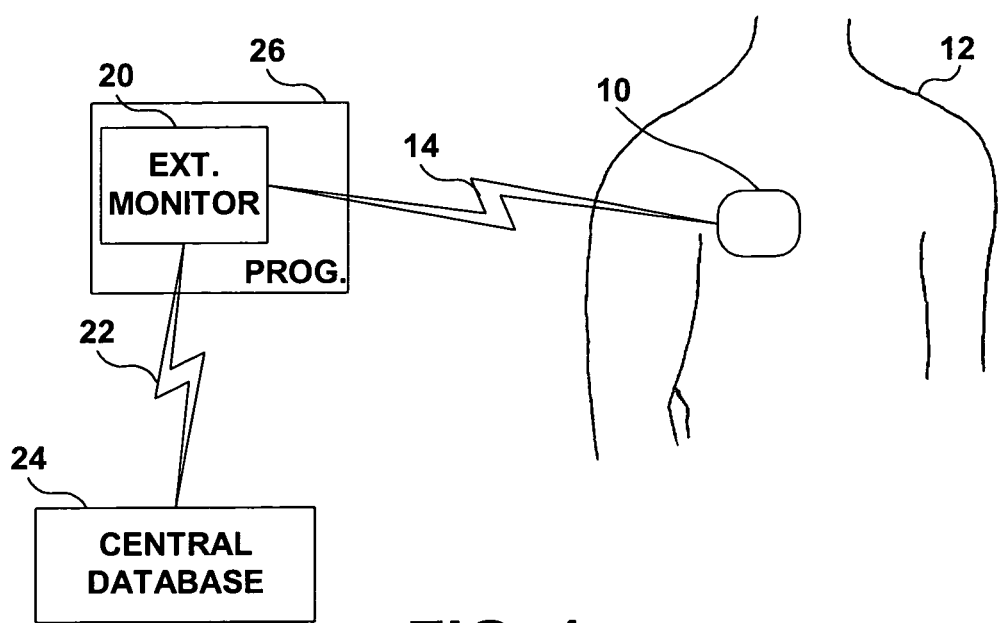
FIG. 1 is a schematic diagram of an implantable medical device system including an external monitor for communicating with the implantable medical device, according to an embodiment of the present invention.

FIG. 1 illustrates an IMD system including an external monitor for communicating with the IMD. IMD 10 is shown implanted in a patient 12. The simplified illustration of IMD 10 may represent a variety of IMDs such as cardiac pacemakers, implantable cardioverter defibrillators, hemodynamic monitors, ECG recorders, drug delivery devices, insulin monitors or pumps, or neuromuscular stimulators. IMD 10 may be coupled to one or more leads or fluid delivery catheters. Leads may be used for carrying electrodes or physiological sensors used for monitoring one or more physiological conditions and delivering electrical stimulation therapies. IMD 10 may alternatively be embodied as a leadless device wherein sensors or electrodes are incorporated in or on the housing of IMD 10. Examples of leadless monitoring devices are generally disclosed in U.S. Pat. No. 5,404,877 issued to Nolan et al., and U.S. Pat. No. 5,987,352 issued to Klein et al., incorporated herein by reference in their entireties.

IMD 10 is provided with an antenna and associated circuitry, as will be described below, for establishing a communication link 14 with external monitor 20. External monitor 20 may be embodied as a dedicated device for communicating with IMD 10 and performing patient alert functions as will be described herein. Alternatively, external monitor 20 may be implemented as a component of a home programmer or monitoring unit 26 which includes other IMD programming and interrogation functions. Programmer and home monitoring units for use with an IMD are known in the art.

As will be described in greater detail herein, patient alert information can be transferred to the external monitor 20 from IMD 10 through bi-directional communication link 14. External monitor 20 may optionally be adapted to communicate with a central database 24 to allow transfer of patient alert data and any other physiological or device-related data received from IMD 10 to the central database 24. Central database 24, also referred to herein as "remote patient management database," may be an Internet-based or other networked database used for remote patient monitoring. External monitor 20 may transfer data via a communication link 22, which may be established via the Internet, a local area network, a wide area network, a telecommunications network or other appropriate communications network and may be a wireless communication link. Examples of remote monitoring systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al.

Figure 2:
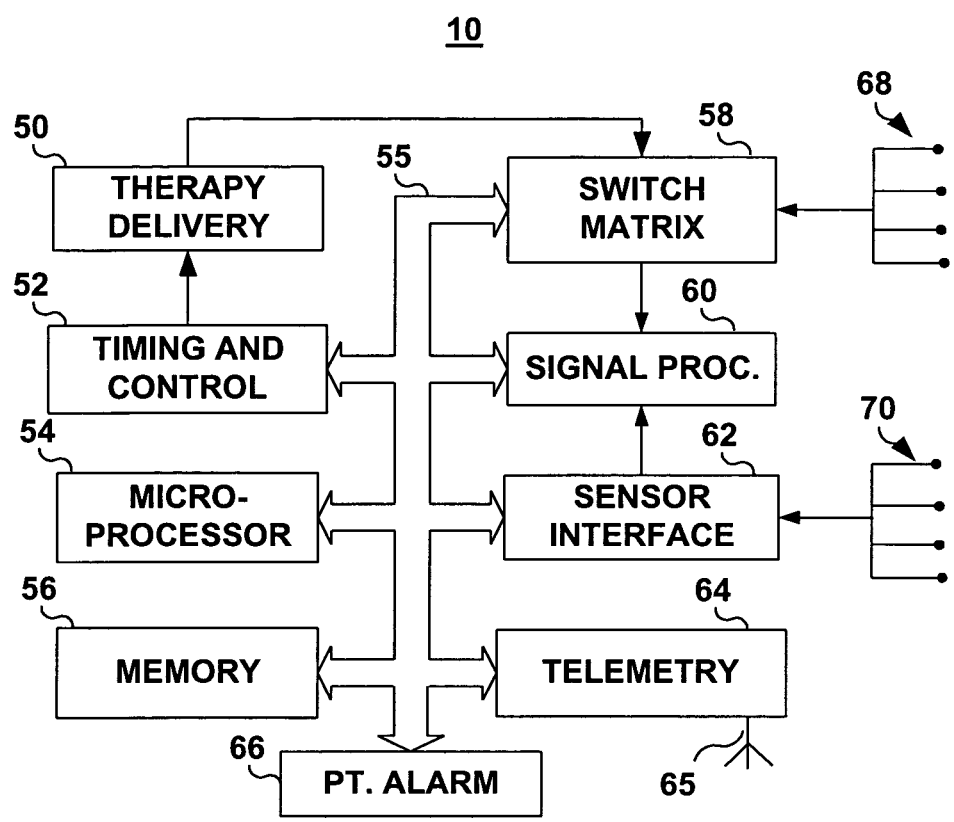
FIG. 2 is an exemplary block diagram of typical functional components of the implantable medical device of FIG. 1.

FIG. 2 is a block diagram of typical functional components of an IMD, such as IMD 10 shown in FIG. 1. IMD 10 generally includes timing and control circuitry 52 and an operating system that may employ microprocessor 54 or other operating system architecture such as a digital state machine for timing sensing and therapy delivery functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may also be used for sensing electrical signals within the body, such as cardiac signals, or for measuring impedance. In the case of cardiac stimulation devices, cardiac electrical signals are sensed for determining when an electrical stimulation therapy is needed and in controlling the timing of stimulation pulses. In some embodiments, detection of an arrhythmia is a patient alert condition, causing IMD 10 to issue a patient alert signal.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog to digital converter. Electrical signals may then be used by microprocessor 54 for detecting physiological events, such as detecting and discriminating cardiac arrhythmias. In other embodiments, electrodes 68 may be used for measuring impedance signals for monitoring edema, respiration or heart chamber volume. Any of these signals may be used to detect a change or level indicating a worsening pathologic condition, which may trigger a patient alert signal. Impedance signals can also be used for monitoring lead performance and detecting lead-related problems as is known in the art.

IMD 10 may additionally or alternatively be coupled to one or more physiological sensors 70. Such sensors may include pressure sensors, accelerometers, flow sensors, blood chemistry sensors, activity sensors or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, or patient activity. Monitored signals may be used for sensing the need for delivering a therapy under control of the operating system. Physiological events or changes in monitored physiological conditions may be defined as triggering conditions for a patient alert signal to be generated by IMD 10.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. All of these functions and operations are known in the art, and generally employed to store operating commands and data for controlling device operation and for later retrieval to diagnose device function or patient condition. In accordance with one embodiment of the invention, parameter values, limits or ranges defining one or more alert trigger conditions may be stored in memory 56 and used by microprocessor 54 in detecting an alert level.

IMD 10 further includes telemetry circuitry 64 and antenna 65. Programming commands or data are transmitted during uplink or downlink telemetry between IMD telemetry circuitry 64 and external telemetry circuitry included in the external monitor. Telemetry circuitry 64 and antenna 65 may correspond to telemetry systems known in the art. Upon detection of a predefined alert level of a physiological or device-related parameter, IMD 10 initiates a telemetry session with the external monitor. Data is transmitted to the external monitor corresponding to the monitored parameter causing the alert condition. Transmitted data may include any other available physiological or device-related data and time and date information.

Telemetry circuitry 64 is embodied as a long range telemetry system that allows alert data to be transferred automatically when it is available without intervention by the patient. Long-range telemetry systems are generally disclosed in U.S. Pat. No. 6,482,154 issued to Haubrich et al., incorporated herein by reference in its entirety. In other embodiments, telemetry circuitry may require patient intervention to initiate or enable transfer of patient alert data to an external monitor. For example, telemetry circuitry 64 may require the use of an external programming head containing an external antenna to be positioned over IMD 10 as generally disclosed in U.S. Pat. No. 5,354,319 issued to Wybomy et al. Telemetry circuitry 64 may require manual "waking up" by the patient to enable data transmission or may require the patient to be within a limited communication range from the external monitor. In such embodiments, IMD 10 includes a patient alarm 66 for notifying the patient that data is ready to be transmitted to the external monitor.

IMD 10 may be equipped with patient alarm circuitry 66 for generating audible tones, a perceptible vibration, muscle stimulation or other sensory stimulation for notifying the patient that a patient alert condition has been detected by IMD 10 and a data transmission is pending. The patient is previously advised to initiate a communication session between the IMD 10 and the external monitor upon perceiving a sensory patient alarm. As such, in some embodiments, the generation of a patient alert signal upon detection of triggering condition causes IMD 10 to generate a sensory patient alarm by alarm 66 and prepare for or automatically initiate a patient alert data transmission via telemetry circuitry 64 to the external monitor.

A patient alert condition may be defined with regard to any of the monitoring functions provided by the IMD 10. The operating system of IMD 10 performs a comparative analysis of sensed signals, or parameters derived there from, to determine if predefined alert triggering conditions are present. If a predefined trigger condition is detected, a patient alert trigger signal is generated. In one embodiment, the patient alert trigger signal causes IMD 10 to "wake up" telemetry circuitry 64 to automatically transfer patient alert data to external monitor 20 via telemetry link 14 (shown in FIG. 1). Additionally, the patient trigger alert signal may cause patient alarm 66 to generate sensory stimulation to the patient. Alternatively, a patient alert trigger signal causes patient alarm 66 to generate sensory stimulation such that the patient initiates a patient alert data transfer to external monitor 20.

Figure 3:
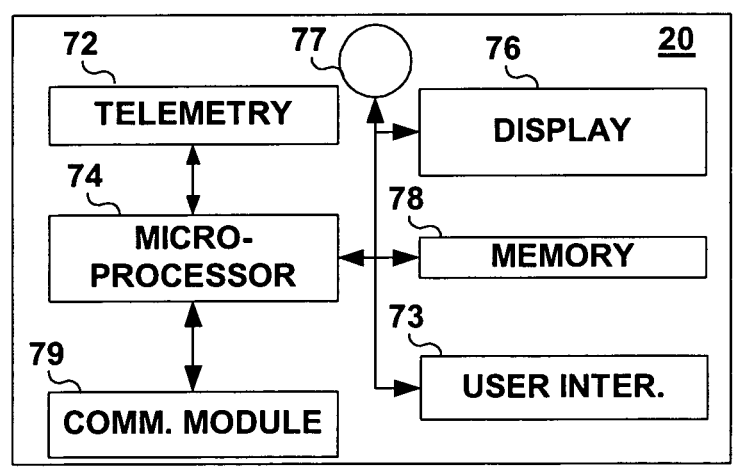
FIG. 3 is a functional block diagram of an external monitor.

FIG. 3 is a functional block diagram of an external monitor 20. External monitor 20 will typically include a telemetry circuit 72 for receiving data from IMD 10. External monitor 20 may be a microprocessor-controlled device wherein microprocessor 74 operates with associated memory 78 for controlling monitor functions. In response to an alert condition data transmission received from IMD 10, microprocessor 74 will schedule at least one subsequent interrogation session for retrieving data from IMD 10 at a future time. In this way, external monitor 20 retrieves updated values for the monitored parameter that triggered the alert condition.

In response to an alert data transmission from IMD 10 and any subsequent scheduled interrogation sessions, external monitor 20 may generate a message on display 76. The message will contain information based on the alert data received from IMD 10 and updated monitor parameter values. External monitor 20 may further include a speaker 77 for generating audible sounds to notify the patient that a transmission has occurred and/or an alert message is being displayed. Display 76 may be a graphical screen allowing for textual or graphical displays. Alternatively display 76 may include LEDs for indicating the presence of an alert condition.

External monitor 20 may include a communications module 79, which may be embodied as a modem, to allow data transmission via a communication network. External monitor 20 may transmit data to a remote patient management database or place a telephone call or send electronic messages to notify the patient, caregivers or medical personnel of the presence of an alert condition and updated parameter values obtained during subsequently scheduled interrogation sessions.

In some embodiments, external monitor 20 includes a user interface 73 for entering commands or programming information if external monitor 20 is enabled to perform programming functions. User interface 73 may be used to manually trigger a data transmission to a communication network via communication module 79 and/or a data retrieval from IMD 10 via telemetry circuit 72.

Figure 4:
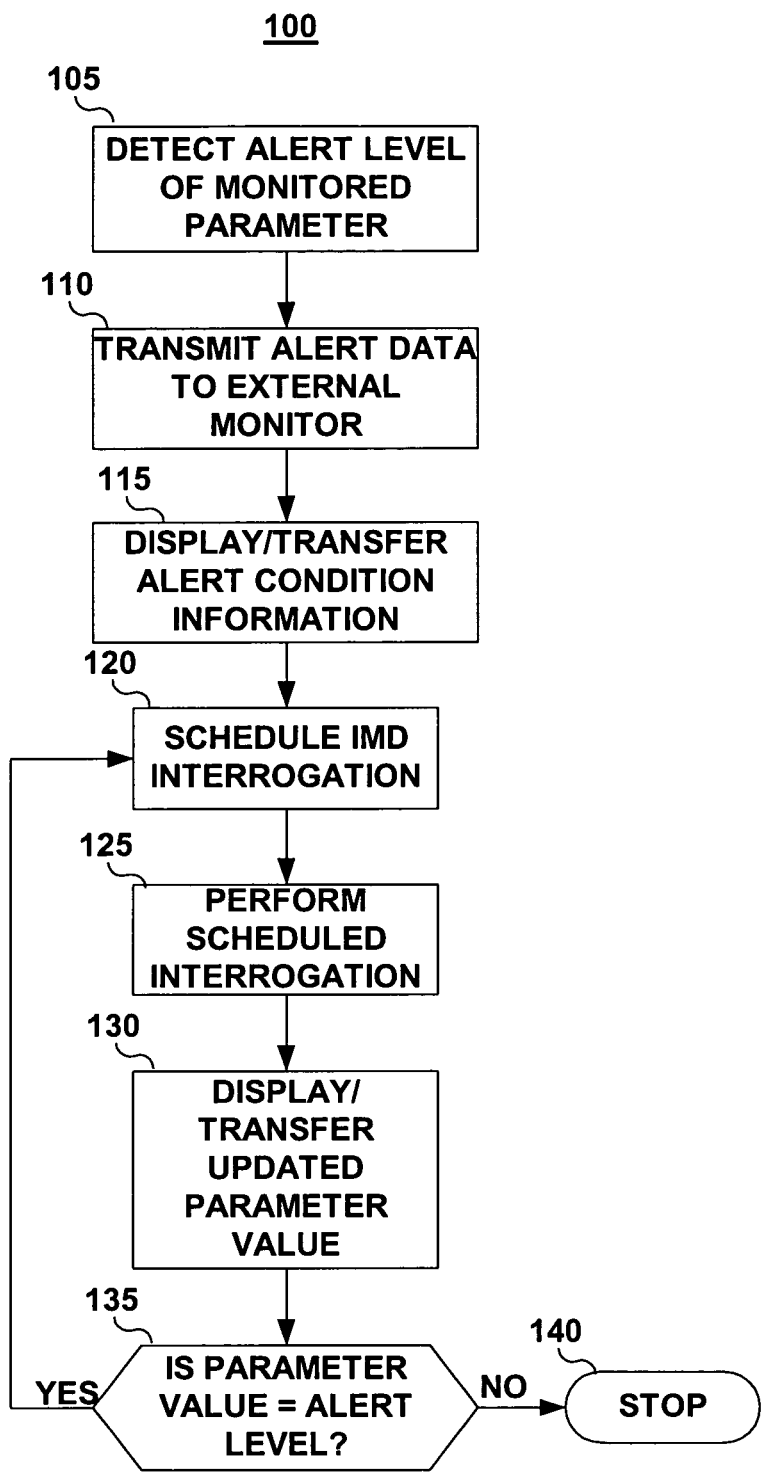
FIG. 4 is flow chart of a method for providing an updated status of a parameter monitored by an implantable medical device according to an embodiment of the present invention.

FIG. 4 is flow chart summarizing a method for providing an updated status of a parameter monitored by an IMD according to an embodiment of the present invention. At step 105, the IMD detects a predefined alert level of a monitored parameter. Method 100 may be applied to any parameter monitored by the IMD, which may include device-related parameters and physiological parameters. An alert level may be a predefined value, range of values, or threshold crossing of the monitored parameter. Alert conditions may be defined for multiple parameters such that method 100 may be invoked by detecting an alert level of more than one monitored parameter and may be operating simultaneously for providing an updated status of multiple monitored parameters.

At step 110, the IMD responds to the detected alert level by transmitting data relating to the alert level detection to the external monitor. The transmitted data may be a signal indicating that an alert level has been detected and indicating the corresponding monitored parameter. In some embodiments, the transmitted data may include actual parameter values, a history of parameter values, other monitored parameter values, time and date information or any other relevant data.

At step 115, the external monitor may display alert data information to inform the patient or another caregiver of the alert condition. As described previously, the display may be an LED display indicating the presence of the alert condition. In various embodiments, the number or color of LEDs illuminated may be used to indicate the severity of the alert condition or the type of alert condition detected. In other embodiments the display may include graphical or textual display on a monitor and/or a broadcast audible sound or voiced message. It is appreciated that numerous variations for displaying or broadcasting alert condition information to a patient or other caregiver may be implemented.

The external monitor may additionally or alternatively transfer alert condition data to a remote patient management database at step 115 via a communication network. Medical personnel may then respond appropriately to the alert condition.

At step 120, the external monitor responds to the alert condition data receipt by scheduling a future IMD interrogation. The IMD interrogation may be scheduled to occur at any time interval, for example after several minutes, several hours, one day, or one week. The appropriate time interval may depend on the type of monitored parameter for which the alert level detection was made. For example, an arrhythmia condition may change over the course of seconds or minutes but an edema condition may change over the course of a day. Some parameters may be monitored in a continuous manner by the IMD such that any time a follow-up interrogation is performed by the external monitor, an updated parameter value will be obtained. Other parameters may be monitored on a periodic basis by the IMD. A scheduled interrogation by the external monitor should therefore occur after the next periodic measurement is expected in order to obtain an updated parameter value. If the monitoring interval is unknown by the external monitor, interrogations may be repeated until an updated parameter value is obtained.

The time interval for scheduling follow-up interrogations for a particular monitored parameter may also be tailored according to individual patient need. Some patients may be at greater risk for requiring hospitalization or emergency care following an alert level. As such, frequent follow-up interrogations may be scheduled to closely monitor a parameter that has reached an alert level.

A patient may respond to the alert notification by taking or adjusting a medication, adjusting his/her activity level, adjusting fluid intake, or taking any other physician-directed action. The patient's response may resolve the condition that caused the alert level detection without requiring the patient to go to a clinic or other medical facility. Scheduling follow-up interrogation sessions by the external monitor allow the patient or other caregiver to observe whether a patient's response to the alert have had a beneficial effect. By scheduling the interrogation sessions at an appropriate frequency, the patient can seek medical attention in a timely manner when the condition is not quickly resolved by the patient's own response to the alert notification. Hospitalization or other serious consequences may thereby be avoided.

In some embodiments, the alert data is transmitted to a remote patient management system and may not be displayed to notify the patient of the condition. Medical personnel may then advise the patient appropriately and continue to monitor the status of the condition via the scheduled follow-up interrogation. Medical personnel can make informed decisions regarding the appropriate time to intervene based on an up-to-date status of the monitored parameter retrieved during scheduled follow-up interrogations.

In another embodiment, scheduling of a follow-up IMD interrogation session at step 120 may be performed through programming operations initiated by the remote patient management system. A programming request may be sent back to the external monitor in response to receiving the alert data by the remote patient management database. The external monitor responds by transferring the scheduled interrogation session data to the IMD.

At step 125, the scheduled interrogation is performed. The external monitor initiates the interrogation session by transferring an interrogation command to the IMD. As described previously, the scheduled interrogation session may not require patient intervention and occur automatically through a long-range telemetry system. The IMD will "wake up" the IMD telemetry circuitry upon the expiration of timers set according to the scheduled interrogation session and is thereby enabled to receive the interrogation request. In other embodiments, the patient or another caregiver may be required to intervene to ensure the IMD telemetry circuitry is enabled and the IMD is within telemetry range of the external monitor for a scheduled, follow-up interrogation.

During the follow-up interrogation, data corresponding to the monitored parameter that caused the previous alert level detection is uplinked to the external monitor. In particular, updated monitored parameter values and/or the status of the alert condition are retrieved. Other data, such as other device-related or physiological parameter data, time and data information, or other relevant data may optionally be retrieved.

At step 130, the updated monitored parameter data is displayed by the external monitor and/or transferred to a remote patient management center. At decision step 135, a determination is made whether the updated parameter value remains at an alert level. If so, another follow-up interrogation session is scheduled at step 120. If the parameter value has returned to a non-alert level, method 100 may be terminated at step 140. The patient and/or medical personnel have been notified at step 130 of the non-alert status of the monitored parameter and further follow-up interrogations are no longer needed. Alternatively, one or more additional follow-up interrogations may be scheduled after detecting a non-alert level of the monitored parameter to ensure that the monitored parameter remains at a non-alert level for a predetermined interval of time.

Figure 5:
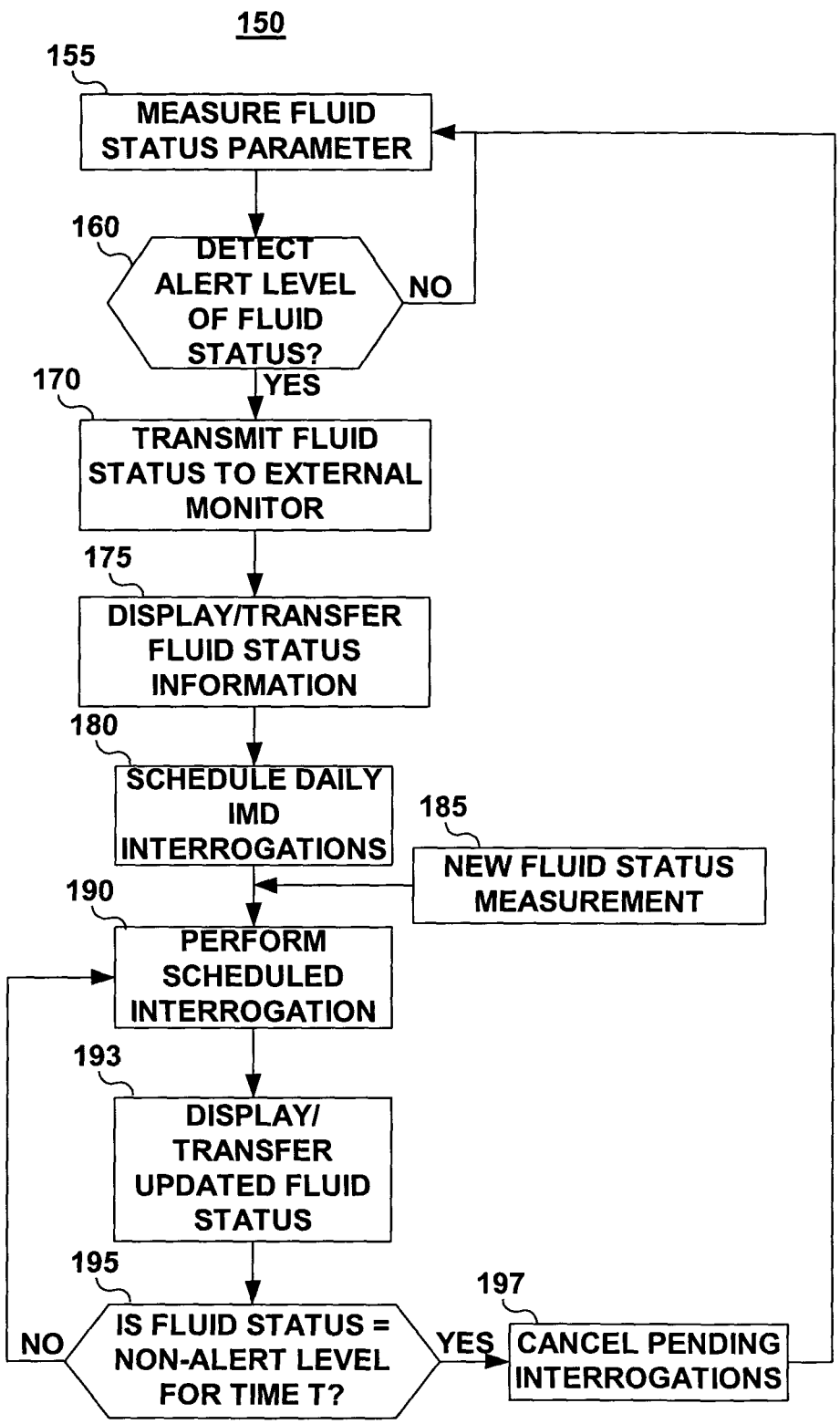
FIG. 5 is a flow chart of a method for providing an updated fluid status on an external monitor according to an embodiment of the present invention.

FIG. 5 is a flow chart summarizing a method for providing an updated fluid status on an external monitor. Patients suffering from congestive heart failure can develop pulmonary edema. Such patients are often medicated with diuretics to manage the fluid level. Careful monitoring of a patient's lung wetness can help in managing the diuretic therapy and prevent severe cases of pulmonary edema which would require hospitalization. As such, in one embodiment of the invention, an updated fluid status parameter is retrieved through scheduled follow-up interrogations following detection of an alert level of the fluid status. By providing an updated fluid status for the patient, the patient or clinician can take appropriate action to address an edemic or over-diuresed condition in a timely manner.

At step 155, a fluid status parameter is measured by the IMD. Generally, measurement of a fluid status parameter includes monitoring an impedance signal for detecting a change in thoracic impedance relating to a change in lung wetness, which may be discerned through evaluation of a change in respiration. Edema monitoring methods may be embodied as generally disclosed, for example, in U.S. Pat. No. 6,512,949 issued to Combs, et al., hereby incorporated herein by reference in its entirety. Other methods known for use in IMDs for detecting changes in lung wetness may be substituted.

At step 160, method 150 determines if the measured fluid status parameter value is at an alert level. An alert level may indicate a low fluid status which may be associated with an over-diuresed condition. Another alert level may indicate a high fluid status associated with an edemic condition. As such more than one alert level may be defined for any monitored parameter indicating different types of physiological conditions that can be indicated by the monitored parameter.

If the measured fluid status parameter value is not at an alert level, the IMD continues measuring the fluid status parameter at step 155 according to the programmed monitoring mode. If an alert level is detected at step 160, the IMD initiates a data transmission at step 170. The fluid status parameter data is transferred to the external monitor. At step 175 alert condition information may be displayed by the external monitor and/or transferred to a remote patient management database. In one embodiment, an LED display on the external monitor may indicate to the patient that the fluid status is at an alert level. One color of LED may be illuminated to indicate a low fluid status alert condition; a different color of LED may be illuminated to indicate a high fluid status condition. Other parameter data or information may optionally be displayed on a screen or broadcast by the external monitor.

The external monitor automatically responds to the receipt of a fluid status alert transmission by scheduling a future IMD interrogation at step 180. In some embodiments, a series of IMD interrogations may be scheduled occurring at an appropriate time interval. For example, in order to provide an updated fluid status, the external monitor may schedule a series of daily IMD interrogations as indicated by step 180. The series of IMD interrogations may be scheduled to occur at a selected time interval for an indefinite period of time or a predetermined number of IMD interrogations may be scheduled.

At step 190, the scheduled, follow-up IMD interrogation is performed to retrieve a new fluid status parameter measurement that has been obtained at step 185, prior to the follow-up interrogation. Information relating to the new fluid status parameter value may be displayed or broadcast by the external monitor and/or transferred to a remote patient management database at step 193. At step 195, the external monitor determines if the fluid status parameter is at a non-alert level. The external monitor may further determine if the parameter has remained at a non-alert level for a predefined interval of time. For example, the external monitor may determine if the fluid status parameter has been at a non-alert level for at least 24 hours or for two successive follow-up interrogations. If not, the next scheduled interrogation is performed at step 190.

Once the fluid status is determined to be at a non-alert level, which may be required for a predefined interval of time or number of successive follow-up interrogations, any pending follow-up interrogations are cancelled at step 197. Method 150 returns to step 155 to continue IMD measurements of the fluid status parameter. In some cases, a scheduled series of follow-up interrogations may expire prior to the monitored parameter reaching a non-alert level at which time the patient and/or medical personnel may take appropriate action.

Some of the techniques described above may be embodied as a computer-readable medium comprising instructions for a programmable processor such as a microprocessor. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

Thus an IMD system and associated method for providing an updated status of a monitored parameter have been presented in the foregoing description with reference to specific embodiments. It is appreciated that various modifications to the referenced embodiments may be made without departing from the scope of the invention as set forth in the following claims.

The invention claimed is:

1. A method for monitoring a physiological parameter of a patient detected by an implantable medical device system comprising an implantable medical device, an external device and a processor configured to perform the method, comprising the steps of:
   monitoring the physiological parameter with the implantable medical device to determine if the physiological parameter exceeds an alert threshold and if the physiological parameter returns to a non-alert level;
   if the physiological parameter exceeds an alert threshold:
      scheduling a series of interrogation sessions between the implantable medical device and the external device to occur at predetermined time intervals;
      transmitting data corresponding to the physiological parameter from the implantable medical device to the external device; and
      continuing monitoring the physiological parameter with the implantable medical device; then
   if the physiological parameter has returned to a non-alert level:
      automatically canceling at least one pending scheduled interrogation session of the series of interrogation sessions; and
      automatically returning to the monitoring the physiological parameter with the implantable medical device; and
   initiating transmitting data step by the external device "waking up" the implantable medical device.

2. The method as in claim 1 wherein the canceling step cancels all pending scheduled interrogation sessions of the series of interrogation sessions.

3. The method as in claim 1, further comprising the step, if the physiological parameter exceeds an alert threshold, of providing an alert to a user.

4. The method as in claim 1 wherein the transmitting step occurs during each of the interrogation sessions.

5. The method as in claim 1, further comprising the step of displaying information relating to the physiological parameter on a user interface.

6. The method as in claim 1, further comprising the step of uploading information relating to the physiological parameter to a remote patient management database.

7. The method as in claim 6 wherein the scheduling step occurs in the remote patient management database.

8. A system, comprising:
   an implantable medical device;
   a sensor which detects a physiological parameter;
   an implantable telemetry interface operatively coupled to the sensor;
   an external device, comprising:
      a monitor telemetry interface, configured to establish a telemetry connection with the implantable telemetry interface;
      the external device configured to initiate transmission of data corresponding to the physiological parameter from the implantable medical device to the external device by "waking up" the implantable medical device; and
   a processor configured to:
      determine if the physiological parameter exceeds an alert threshold and if the physiological parameter returns to a non-alert threshold;
      schedule a series of interrogation sessions of the implantable medical device to occur at a plurality of predetermined time intervals if the physiological parameter exceeds an alert threshold; and then
      if the physiological parameter has returned to a non-alert level:
         automatically cancel at least one pending interrogation session of the series of interrogation sessions.

9. A system as in claim 8 wherein the processor automatically cancels all pending interrogation sessions of the series of interrogation sessions.

10. A system as in claim 8, further comprising an implantable medical device, wherein the implantable medical device comprises the sensor and the implantable telemetry interface.

11. A system as in claim 10 wherein the implantable medical device further comprises a device electronic componentry operatively coupled to the sensor;
   the external monitor further comprises the processor operatively coupled to the monitor telemetry interface; and
   wherein the device electronic componentry transmits a value indicative of the physiological parameter to the processor via the telemetry connection.

12. A system as in claim 8, further comprising a user interface, the user interface having:
   an indication of the physiological parameter exceeding the alert threshold;
   an indication of the physiological parameter does not exceed the non-alert threshold; and
   a schedule for a medical professional to schedule the interrogation sessions.

13. A system as in claim 8, further comprising a remote patient management database operatively coupled to the external monitor, wherein the remote patient management database schedules the series of interrogation sessions.

* * * * *